US00PP28855P3

(12) United States Plant Patent
Castillo

(10) Patent No.: US PP28,855 P3
(45) Date of Patent: Jan. 9, 2018

(54) RASPBERRY PLANT NAMED 'SAN RAFAEL'

(50) Latin Name: *Rubus idaeus L.*
Varietal Denomination: SAN RAFAEL

(71) Applicant: Juan Enrique Castillo, Seville (ES)

(72) Inventor: Juan Enrique Castillo, Seville (ES)

(73) Assignee: VIVEROS CALIFORNIA S.L., Seville (ES)

( * ) Notice: Subject to any disclaimer, the term of this patent is extended or adjusted under 35 U.S.C. 154(b) by 0 days.

(21) Appl. No.: 14/545,736

(22) Filed: Jun. 11, 2015

(65) Prior Publication Data

US 2016/0366798 P1 Dec. 15, 2016

(51) Int. Cl.
*A01H 5/08* (2006.01)

(52) U.S. Cl.
USPC ..... Plt./204

(58) Field of Classification Search
USPC ..... Plt./156, 203, 204
See application file for complete search history.

(56) References Cited

U.S. PATENT DOCUMENTS

PP25,245 P3 * 1/2015 Pierron-Darbonne A01H 5/0887 Plt./204

OTHER PUBLICATIONS

PLUTO: Plant Variety Database, Dec. 20, 2016, citation for 'San Rafael'. 1 page.*

* cited by examiner

*Primary Examiner* — Susan McCormick Ewoldt
*Assistant Examiner* — Karen Redden
(74) *Attorney, Agent, or Firm* — Ballew Law

(57) ABSTRACT

A new raspberry plant named 'SAN RAFAEL' is disclosed. The plants of 'SAN RAFAEL' are characterized by the late maturity of fruit, strong shoot growth, and fruiting buds covering the entire length of the fruiting canes.

6 Drawing Sheets

Genus and species: *Rubus idaeus L.*
Variety denomination: 'SAN RAFAEL'.

CROSS-REFERENCE TO RELATED APPLICATIONS

None

STATEMENT REGARDING FEDERALLY SPONSORED RESEARCH OR DEVELOPMENT

None

BACKGROUND OF THE INVENTION

'SAN RAFAEL' is a product of a controlled breeding program by cross pollination of female parent 'Malling Exploit' (Unpatented) and male parent 'Tulameen' (Unpatented), carried out by the inventor in the Geria, in the Andalucia region of Spain. Prior to 2014, the original single plant of 'SAN RAFAEL' was expanded using root sucker propagation to multiple plants, which were planted in the area of Geria, Spain. By 2014, the plants had been observed and evaluated for several years. Throughout several generations of asexual propagation using both root sucker propagation and tissue culture propagation, 'SAN RAFAEL' has been observed to retain its distinctive characteristics and

COMPARISON NEW VARIETY TO THE PARENTS

Male parent 'Tulameen' has a lower yield than 'SAN RAFAEL', and does not tolerate cold temperatures as well as 'SAN RAFAEL'. Both 'Tulameen' and 'SAN RAFAEL' are similar in size and form of the fruit. However, 'SAN RAFAEL' produces higher quality fruit, with a very high yield, which demonstrates very good post-harvest cold storage characteristics.

The plants of female parent 'Malling Exploit' have more thorns than plants of 'SAN RAFAEL'. The fruit of 'Malling Exploit' is smaller in size than the fruit of 'SAN RAFAEL', and fruit of 'Malling Exploit' does not demonstrate the excellent post-harvest storage characteristics of 'SAN RAFAEL'. While the fruit of 'Malling Exploit' and 'SAN RAFAEL' are similar in shape and color, the fruit of 'SAN RAFAEL' is larger and firmer than the fruit of 'Malling Exploit'. The yield of fruit of 'SAN RAFAEL' is also greater than the yield of 'Malling Exploit'. The fruit of 'SAN RAFAEL' keeps well in post-harvest cold storage, and demonstrates good shelf life at ambient temperatures after being taken out of cold storage. The fruit of 'Malling Exploit' does not demonstrate the favorable post-harvest and shelf life characteristics.

COMPARISON NEW VARIETY TO 'GLEN LYON'

'SAN RAFAEL' fruit is of greater size and pyramidal shape whereas 'Glen Lyon' (unpatented) shape of fruit is round. 'SAN RAFAEL' has better organoleptic characteristics, better taste and aroma than 'Glen Lyon'. 'SAN RAFAEL' requires about 1,000 artificial cold hours in cold rooms in areas where the plants have been tested (Huelva, Spain), sprouting all the buds from top to bottom, showing greater budding capacity than 'Glen Lyon'. 'SAN RAFAEL' flowering occurs in 25% of foliage emergence, showing wider and more productive lateral branches than 'Glen Lyon'. The plants of 'SAN RAFAEL' are more vigorous and vegetative than the 'Glen Lyon' variety. The 'SAN RAFAEL' variety is classified as a floricane variety because it fruits on second year wood. In all trials, it begins to fructify about 10 days before 'Glen Lyon'. The fruit of 'SAN RAFAEL' is large in size and the average fruit weight is approximately 15-20% more than a fruit of 'Glen Lyon'. The fruit of 'SAN RAFAEL' measures on average between 3 and 3.5 cm in length and 2-2.5 cm in width, presenting a conical-elongated shape, in comparison to the cylindrical shape of fruit of 'Glen Lyon'. The fruit of 'SAN RAFAEL' demonstrates excellent post-harvest storage characteristics, maintain good firmness without bleeding.

BRIEF DESCRIPTION OF THE PHOTOGRAPHS

Figure 1:
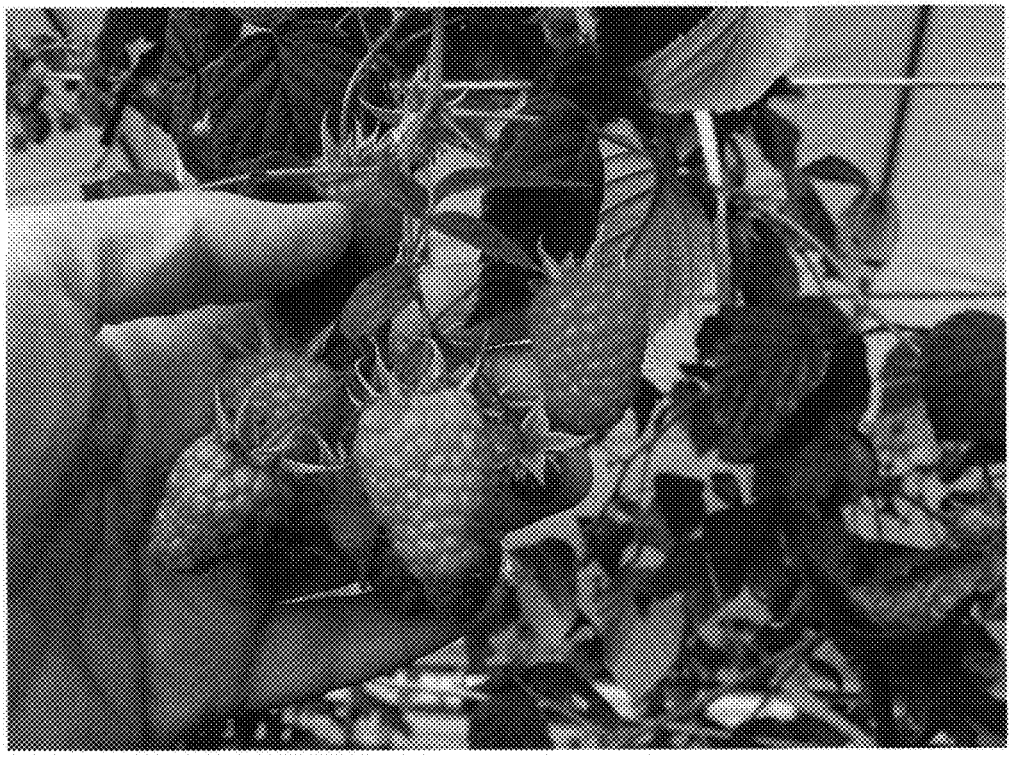
FIG. 1 illustrates fruit in various stages of maturity of a mature 'SAN RAFAEL' raspberry plant.
Figure 2:
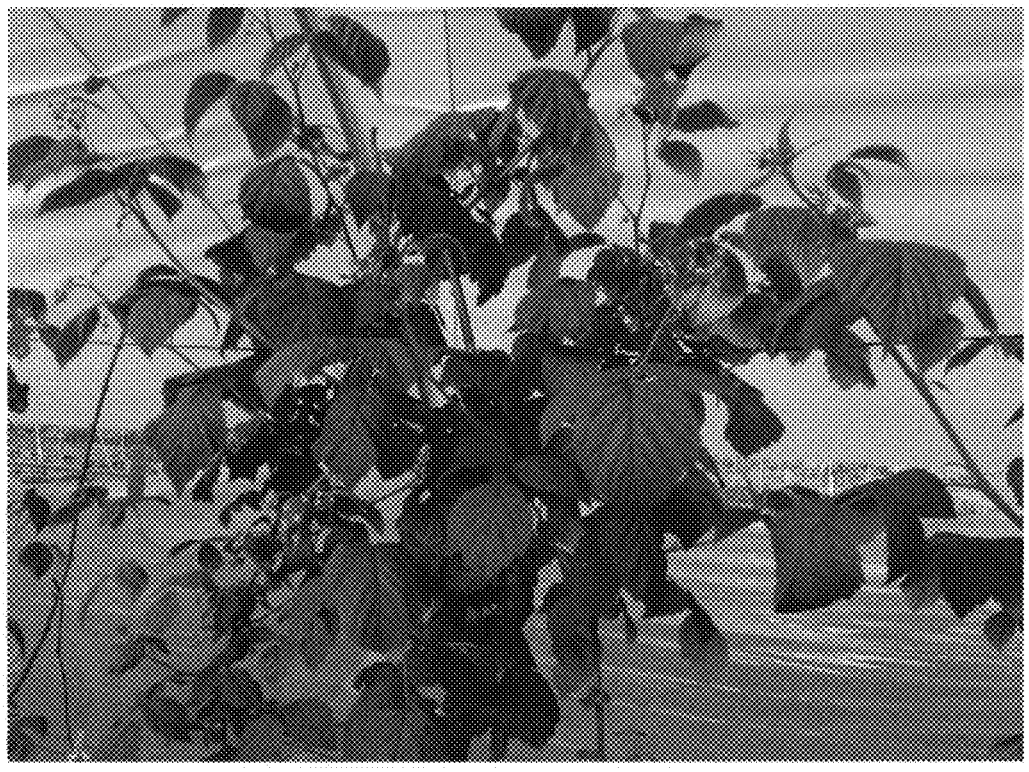
FIG. 2 illustrates a mature 'SAN RAFAEL' raspberry plant with fruit buds.
Figure 3:
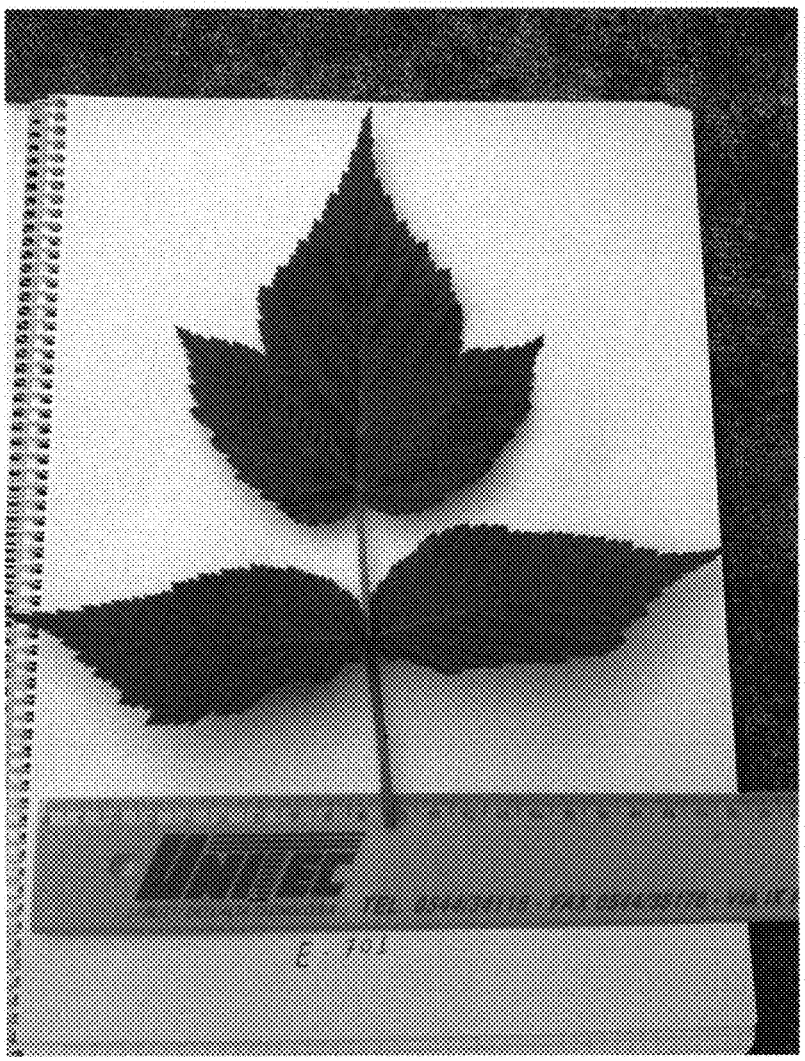
FIG. 3 illustrates a leaf of a mature 'SAN RAFAEL' raspberry plant.
Figure 4:
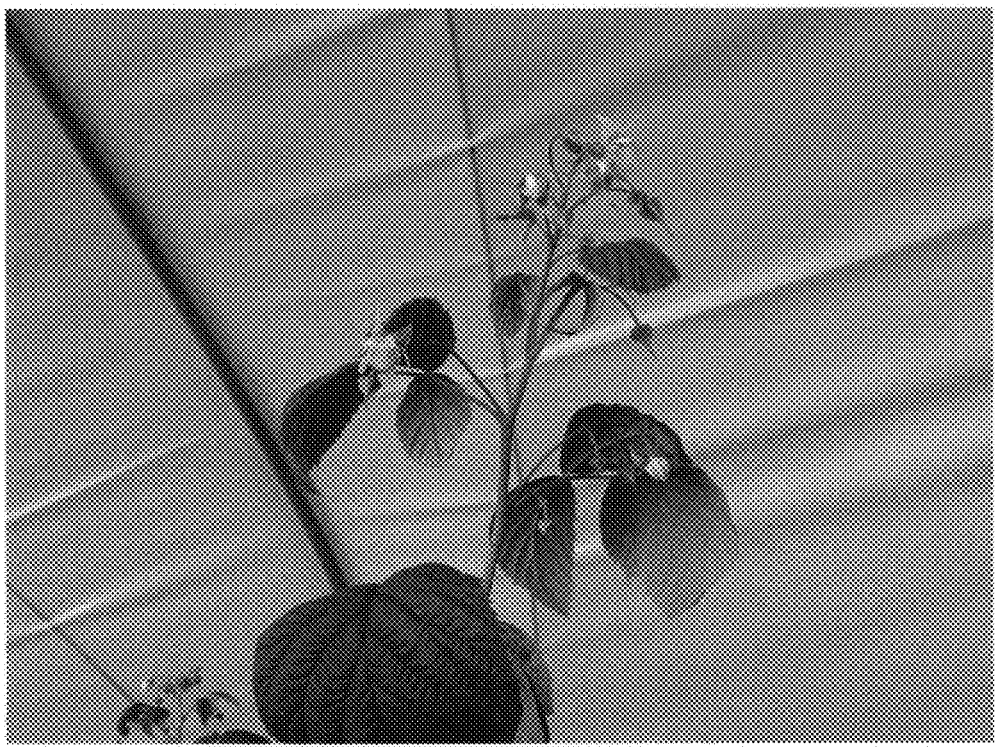
FIG. 4 illustrates flowers of a mature 'SAN RAFAEL' raspberry plant.
Figure 5:
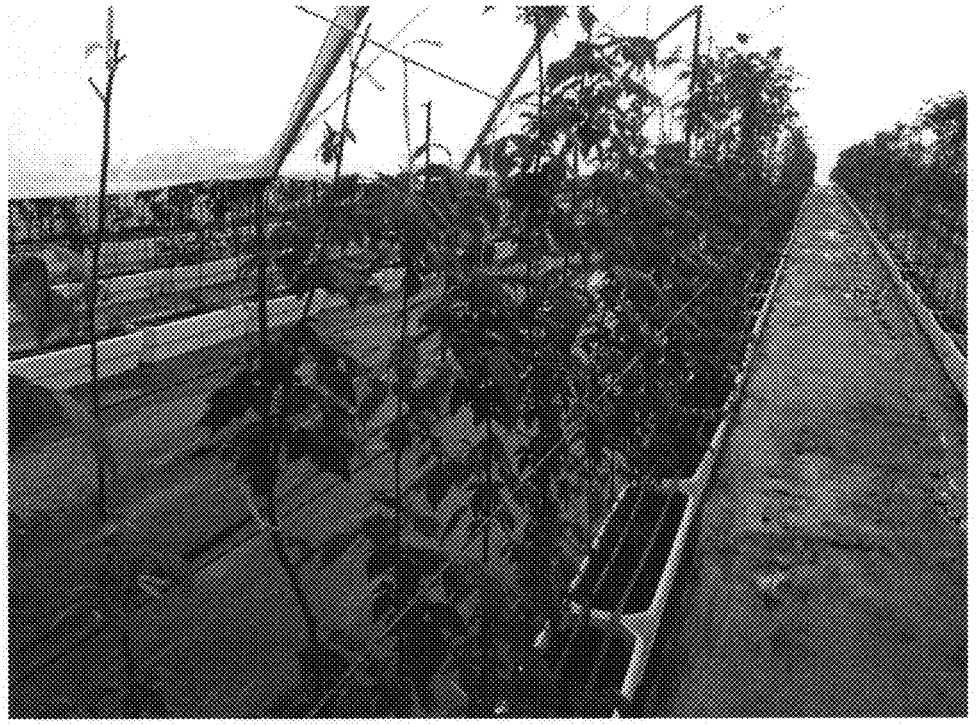
FIG. 5 illustrates vines of mature 'SAN RAFAEL' raspberry plants growing on a trellis system.
Figure 6:
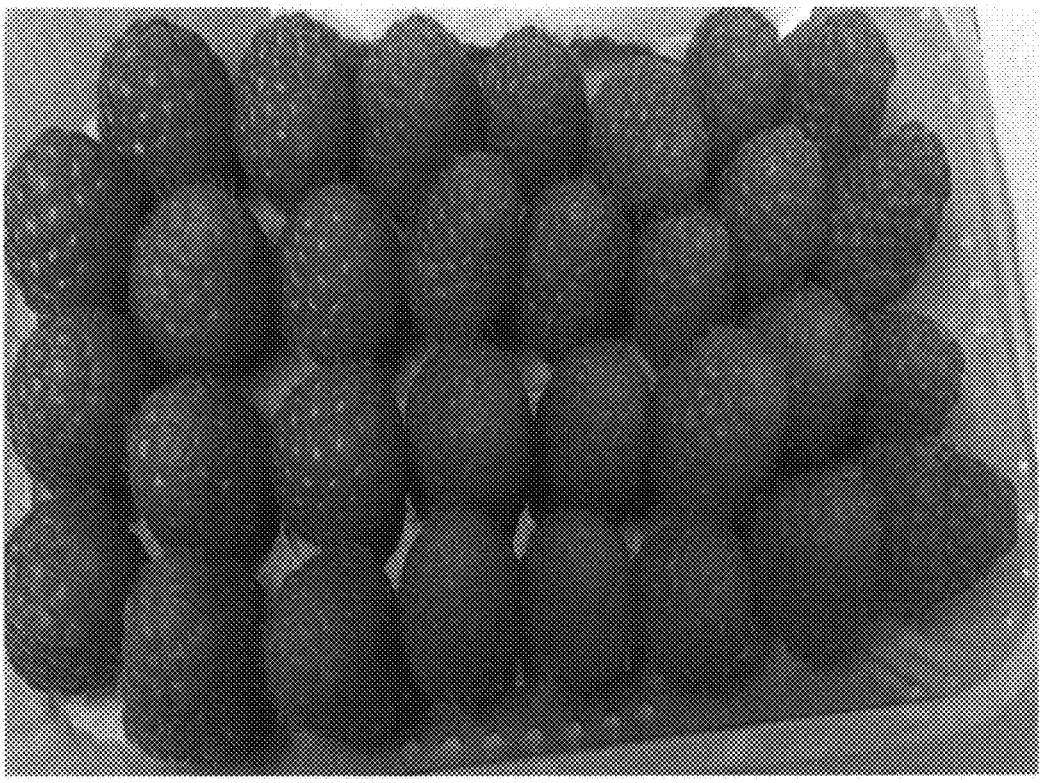
FIG. 6. Illustrates fully mature, harvested fruit from 'SAN RAFAEL' raspberry plants.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2013 and 2014 growing seasons in the Andalucia region of Spain. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. The measurements used in botanical description are from plants that are approximately 125 day old. All color references are based on The Royal Horticultural Society Color Chart, $6^{th}$ edition published in 2015.

Use: To produce raspberry fruit for the fresh and processed markets.

Number of current season's canes: Medium (similar to 'Glen Ample' (U.S. Plant Pat. No. 11,418), 'Multiraspa' (unpatented), and 'Rumiloba' (unpatented)).

Anthocyanin coloration of apex during rapid growth of very young shoot: This characteristic is absent (similar to 'Gelbe Antwerpener' (unpatented)).

Spines present: Yes (similar to 'Malling Promise' (unpatented)).

General fruit shape in lateral view: Trapezoidal (similar to 'Gradina' (unpatented)).

Fruit bearing characteristics: Fruit is present only on previous season's cane in the summer (similar to 'Malling Promise').

Time of beginning of fruit ripening on previous season's canes: Late (similar to Malling Landmark, Schönemann).

Plant:
- *Habit.*—Floricane.
- *Length.*—1.80 cm.
- *Width.*—1.20 cm.

Cane:
- *Length.*—1.80 cm.
- *Diameter.*—2.5 cm.
- *Texture.*—Thorny.
- *Color.*—Moderate Brown 200C.

Leaves:
- *Arrangement.*—Opposite.
- *Vein color.*—Yellow Green 144B.
- *Venation.*—Pinnate.
- *Shape.*—Compound leaf, imparipinnate.
- *Length.*—22 cm.
- *Width.*—16 cm.

Leaflets:
- *Shape.*—Elliptical shape with serrated margins.
- *Texture.*—Glabrous.
- *Length.*—12-14 cm.
- *Width.*—6-7 cm.
- *Upper color.*—Moderate Yellowish Green 137A.
- *Lower color.*—Brown Green N148B.

Spines:
- *Shape.*—Pyramidal.
- *Length.*—2 mm.
- *Width.*—0.5 mm.
- *Color.*—Dark Grayish Reddish Brown 200A.

Bud:
- *Location.*—Huelva, Spain.
- *Bud burst.*—20 days after transplant.
- *Bloom time.*—60 days after transplant.
- *Harvest.*—90 days after transplant.
- *Size.*—1 cm.
- *Color.*—Moderate Brown 200C.
- *Shape.*—Pyramidal.

Sepal:
- *Color.*—Brilliant Yellowish Green 142B.
- *Texture.*—Pubescent.
- *Average length.*—1.5 cm.
- *Width.*—0.5 cm.

Flower:
- *Diameter.*—1.3 cm.
- *Presence or absence of fragrance.*—Present.
- *Average number of flowers per panicle.*—4.

Petal:
- *Number of petals per flower.*—5 petals.
- *Shape.*—Lanceolate.
- *Length.*—0.8 cm.
- *Width.*—0.5 cm.
- *Texture.*—Glabrous.
- *Upper and lower color.*—Very Pale Purple 69C.

Reproductive organs:
- *Stigma color.*—Yellowish White 155D.
- *Style color.*—Yellowish White 155D.
- *Style size.*—2 mm.
- *Ovary color.*—White NN155B.
- *Ovary size.*—5 mm.
- *Stamen color.*—Brownish Red 165A.
- *Stamen size.*—6 mm.

*Anther color.*—White NN155D.
*Anther size.*—0.5 mm.
*Pollen color.*—White NN155D.

Pedicle:
*Length.*—0.9 cm.
*Color.*—Strong Yellowish Green 144B.

Penducle:
*Color.*—Strong Yellowish Green 144B.
*Diameter.*—1.5 mm.
*Thorns.*—Present.

Pollination: Pollination can be achieved by wind (anemophily pollination) as well as insects (entomophily pollination), mainly by bees and bumblebees.

Fruit:
*Shape.*—Trapezoidal.
*Average number of druplets.*—200.
*Skin color.*—Red N45C.
*Flesh color.*—Red N45C.
*Length.*—3 cm.
*Width.*—2 cm.
*Average weight.*—6 g.
*Diameter of hollow center of the fruit.*—1 cm.
*Depth of hollow center of the fruit.*—2.5 cm.
*First fruit ripening.*—January 1$^{st}$.
*Full fruit ripening.*—June 15$^{th}$.
*Productivity.*—700 grams per bush.

Hardiness:
*Winter hardiness.*—High.
*Drought/heat tolerance.*—High.

TABLE 1

| Storage Characteristics: | | | | |
|---|---|---|---|---|
| | Soft | Bleeding | Broken | Color |
| Test 1 (25 pieces of fruit) Apr. 22, 2015 | | | | |
| Initial | 1 | 0 | 0 | Red |
| After 3 days cold | 1 | 0 | 0 | Red |
| After 3 days room | 1 | 0 | 0 | Red |
| Test 2 (25 pieces of fruit) Apr. 28, 2015 | | | | |
| Initial | 0 | 0 | 0 | Red |
| After 3 days cold | 0 | 0 | 0 | Red |
| After 3 days room | 5 | 1 | 0 | Deep Red |
| Test 3 (25 pieces of fruit) May 5, 2015 | | | | |
| Initial | 1 | 0 | 0 | Red |
| After 3 days cold | 2 | 1 | 0 | Red |
| After 3 days room | 5 | 2 | 0 | Deep Red |

What is claimed is:

1. A new and distinct raspberry plant as shown and described herein.

* * * * *